US011980548B2

(12) United States Patent
Tan et al.

(10) Patent No.: US 11,980,548 B2
(45) Date of Patent: May 14, 2024

(54) CARBON FIBER COMPOSITE ARTIFICIAL BONE AND PREPARATION METHOD THEREOF

(71) Applicant: HUNAN TANKANG BIOTECH CO., LTD., Hunan (CN)

(72) Inventors: Zhoujian Tan, Hunan (CN); Jiqiao Liao, Hunan (CN); Xiang Zhang, Hunan (CN); Xu Yi, Hunan (CN)

(73) Assignee: HUNAN TANKANG BIOTECH CO., LTD., Hunan (CN)

( * ) Notice: Subject to any disclaimer, the term of this patent is extended or adjusted under 35 U.S.C. 154(b) by 278 days.

(21) Appl. No.: 16/640,735

(22) PCT Filed: Aug. 17, 2018

(86) PCT No.: PCT/CN2018/100996
§ 371 (c)(1),
(2) Date: Feb. 21, 2020

(87) PCT Pub. No.: WO2019/037657
PCT Pub. Date: Feb. 28, 2019

(65) Prior Publication Data
US 2020/0188117 A1 Jun. 18, 2020

(30) Foreign Application Priority Data
Aug. 23, 2017 (CN) .......................... 201710731455.4

(51) Int. Cl.
*A61F 2/28* (2006.01)
*A61L 27/08* (2006.01)
(Continued)

(52) U.S. Cl.
CPC ................ *A61F 2/28* (2013.01); *A61L 27/08* (2013.01); *A61L 27/306* (2013.01); *D03D 1/00* (2013.01);
(Continued)

(58) Field of Classification Search
CPC .............. A61F 2/28; A61F 2310/00161; A61F 2310/00574; A61F 2002/30563; A61F 2310/574; A61L 27/08; A61L 2430/02
See application file for complete search history.

(56) References Cited

U.S. PATENT DOCUMENTS 3,707,006 A * 12/1972 Bokros ............... A61F 2/30965
433/201.1
5,181,930 A 1/1993 Dumbleton et al.
(Continued)

FOREIGN PATENT DOCUMENTS

CN 1501818 6/2004
CN 102366641 3/2012
(Continued)

OTHER PUBLICATIONS

"International Search Report (Form PCT/ISA/210) of PCT/CN2018/100996," dated Apr. 29, 2019, with English translation thereof, pp. 1-8.

*Primary Examiner* — Christopher D. Prone
(74) *Attorney, Agent, or Firm* — JCIP GLOBAL INC.

(57) ABSTRACT

The invention discloses a carbon fiber composite artificial bone and a preparation method thereof. The artificial bone includes a carbon fiber composite spring-like frame or includes a carbon fiber composite spring-like frame and a carbon fiber composite plate dowel, and the carbon fiber composite plate dowel is inserted into one end or both ends of a cavity of the spring-like frame or penetrates through the cavity of the carbon fiber composite spring-like frame. The preparation method includes: preparing a spring-like carbon fiber preform through a weaving technology by using carbon fibers as a raw material, performing densification and high-temperature purification treatment and preparing a wear-resistant coating to obtain the carbon fiber composite spring-like frame; and combining the carbon fiber composite (Continued)

spring-like frame with the carbon fiber composite plate bowel to obtain the artificial bone.

5 Claims, 1 Drawing Sheet

(51) Int. Cl.
 *A61L 27/30* (2006.01)
 *D03D 1/00* (2006.01)
 *A61F 2/30* (2006.01)
(52) U.S. Cl.
 CPC ........... *A61F 2002/30113* (2013.01); *A61F 2002/30154* (2013.01); *A61F 2002/30187* (2013.01); *A61F 2002/30433* (2013.01); *A61F 2002/30563* (2013.01); *A61F 2310/00161* (2013.01); *A61F 2310/00574* (2013.01); *A61L 2430/02* (2013.01); *D10B 2101/12* (2013.01); *D10B 2509/00* (2013.01)

(56) References Cited

U.S. PATENT DOCUMENTS

| 5,306,310 | A | 4/1994 | Siebels |
| 2009/0187258 | A1* | 7/2009 | Ip .......................... A61L 27/38 623/23.72 |

FOREIGN PATENT DOCUMENTS

| CN | 102718535 | 10/2012 |
| CN | 101416906 | 2/2013 |
| CN | 103271761 | 9/2013 |
| CN | 102764453 | 9/2014 |
| CN | 105246518 | 1/2016 |
| CN | 107518962 | 12/2017 |
| CN | 107536659 | 1/2018 |
| CN | 105477687 | 5/2019 |
| WO | 2007074896 | 7/2007 |
| WO | 2014190289 | 11/2014 |

\* cited by examiner

CARBON FIBER COMPOSITE ARTIFICIAL BONE AND PREPARATION METHOD THEREOF

CROSS-REFERENCE TO RELATED APPLICATION

This is a 371 application of the International PCT application serial no. PCT/CN2018/100996, filed on Aug. 17, 2018, which claims the priority benefits of China Application No. 201710731455.4, filed on Aug. 23, 2017. The entirety of each of the above-mentioned patent applications is hereby incorporated by reference herein and made a part of this specification.

TECHNICAL FIELD

The invention relates to an artificial bone, in particular to a carbon fiber composite artificial bone and a method for preparing the carbon fiber composite artificial bone by using a carbon fiber weaving technology and a profiling technology, and belongs to the field of biomedical materials.

BACKGROUND

Bone defects caused by trauma, tumor, infection and dysplasia have always been an issue troubling medical scientists. Artificial bone transplantation is a common method to treat clinical bone defects currently. At present, artificial bone biomaterials used clinically in the field of orthopedics mainly include metal materials, ceramics and polymer materials, which are included in many literature reports. For example, a patent applied by Japanese in China (application number: CN02807099.2) discloses a porous ceramic artificial bone material formed from β-calcium phosphate, which can be transplanted with bone marrow cells and has good compatibility. A Chinese patent (application number: CN201510928718.1) discloses a porous artificial bone with a honeycomb mesh shape and a preparation method thereof. Raw materials including PLGA and MgSr-TCP are mainly adopted to prepare an MgSr-TCP honeycomb mesh framework by an existing 3D printing method, and then PLGA slurry and nano-scale sodium chloride particles are mixed through vibration, poured into the honeycomb mesh framework, freeze-dried, and oven-dried to obtain the artificial bone. The artificial bone has relatively high hardness and toughness, and good biomechanical property, and the framework can be designed into different shapes to meet personalized requirements, making the product more flexible and smarter. A Chinese patent (application number: CN200810227420.8) discloses preparation of a medical metal artificial bone trabecula, which is mainly prepared by melting titanium alloy powder at a high temperature with electron beam melt-molding equipment. The mechanical and biological characteristics of the metal artificial bone trabecula are similar to those of human bones. The metal artificial bone trabecula has a high surface friction coefficient, a stable structure, and a wide application range, and can be used as a substitute bone for various bone defects, bone filling, bone supporting, bone remodeling and bone reshaping in the human bone system. All the artificial bone implants reported at present have their own advantages, but there are also some obvious disadvantages. For example, metal materials are prone to electrolysis, abrasion, fatigue, looseness, corrosion, bone absorption, artifacts in medical images, etc.; polymer materials have defects such as aging, poor creep resistance, toxic reaction, thrombosis, etc.; and bioceramic materials have no plasticity, are too brittle, get broken easily, etc.

Carbon materials have good biocompatibility, for example, carbon fibers, pyrolytic carbon, carbon nanotubes and composites thereof are applied in heart valves, bones, tendons, growth scaffolds, oncology drugs, biosensors, etc. Especially, carbon/carbon composites with the carbon materials as matrixes and carbon fibers and fabric thereof as reinforcement has the characteristics of light weight, good biocompatibility, good chemical stability, mechanical property similar to that of human bones, good fatigue resistance, strong designability and the like, thus being regarded as an ideal replacement material for an existing artificial bone and gaining popularity among researchers. Many carbon materials have been applied to artificial bones at present. For example, a Chinese patent (CN201110324420.1) discloses that a middle layer structure adopts high-strength carbon fibers; in order to increase hardness and toughness, the carbon fibers are pre-impregnated with phenolic resin to form a composite reinforcing material; and a silicon carbide layer is formed on surfaces of the carbon fibers by means of a gas phase sedimentation method, epoxy resin adheres to the silicon carbide outer layer in the stretching direction of the carbon fibers to form an epoxy resin layer, an HA layer is formed outside the epoxy resin layer through plasma spraying of HA, and an OPG protein layer is arranged outside the HA layer. The artificial bone has the characteristics of high strength, good hardness, good toughness, corrosion resistance, high bearing capacity, good tissue compatibility, high firmness and durability, good plasticity and the like. A Chinese patent (CN201210261732.7) discloses a preparation method of a personalized carbon-carbon composite artificial bone. A carbon fiber reinforced carbon matrix is selected as a raw material, an artificial bone contour is acquired through CT image acquisition, and the acquired artificial bone contour is converted into a non-uniform rational B-spline curved surface to treat the carbon fiber reinforced carbon matrix, so as to form a carbon/carbon composite artificial bone structure; after that, argon gas is introduced into a vacuum glow discharge chamber for plasma pretreatment of the surface of the carbon/carbon composite artificial bone, and then the surface of the carbon/carbon composite artificial bone is sprayed with a hydroxyapatite coating to prepare the personalized carbon/carbon composite artificial bone.

SUMMARY

Technical Problems

Although having the characteristics of light weight, good biocompatibility, good chemical stability, mechanical property similar to that of human bones and the like, these carbon/carbon composites cannot realize elastic deformation, some functions of cartilage and functions such as bending modeling, which limits their application scope.

Solutions to Problems

Technical Solutions

Aiming at the defects of an existing artificial bone prepared from the carbon/carbon composites, one objective of the invention is to provide a carbon fiber composite artificial bone which has light weight, and good biocompatibility and mechanical property, can avoid artifacts in medical images, especially has good elastic deformation property and high toughness, and can realize some functions of cartilage and bending modeling.

Another objective of the invention is to provide a method for preparing the carbon fiber composite artificial bone which has good elastic deformation property and high toughness, and can realize some functions of cartilage and bending modeling by combining a carbon fiber weaving technology and a profiling technology. The method is easy to operate, and beneficial to forming and large-scale production.

In order to achieve the above technical objectives, the invention provides a carbon fiber composite artificial bone, including a carbon fiber composite spring-like frame or including a carbon fiber composite spring-like frame and a carbon fiber composite plate dowel, and the carbon fiber composite plate dowel is inserted into one end or both ends of a cavity of the spring-like frame or penetrates through the cavity of the carbon fiber composite spring-like frame.

The carbon fiber composite artificial bone provided by the invention has a special carbon fiber composite spring-like frame, and the spring-like frame formed by a carbon fiber composite endows the artificial bone with good elastic deformation property, so that the artificial bone can be bent at 360° arbitrarily. The carbon fiber composite plate dowel is arranged at one end or both ends of the cavity of the frame or penetrates through the cavity of the frame. The plate dowel is used as a connecting end of the artificial bone and other tissues and is beneficial to the fixation of the artificial bone, and when arranged in a penetrating mode, the plate dowel can also improve the mechanical property of the artificial bone and enhance the deformation recovery capability of the artificial bone, and the artificial bone with this structure can realize some functions of cartilage and bending modeling.

Preferably, the carbon fiber composite spring-like frame consists of a carbon fiber spring-like frame and a pyrolytic carbon coating, a silicon carbide coating or a pyrolytic carbon/silicon carbide mixed coating on a surface thereof. Preparing the pyrolytic carbon coating, the silicon carbide coating or the pyrolytic carbon/silicon carbide mixed coating on a surface of a carbon fiber material to form the carbon fiber composite is mainly for surface modification of carbon fibers, so as to, for example, improve their wear resistance, increase their biocompatibility, etc.

Preferably, the carbon fiber spring-like frame is of a spring-like structure woven from the carbon fibers.

Preferably, a cross section of the carbon fiber composite spring-like frame is circular, oval, D-shaped, pea-shaped or square.

Preferably, a carbon material pipe casing is arranged outside the carbon fiber composite spring-like frame. After the artificial bone is transplanted into the human body, tissues will grow into the spring-like frame of the artificial bone, thus affecting its deformation. The casing can effectively prevent the occurrence of this situation. The arrangement of the carbon material pipe casing will affect the bending deformation property of the spring-like frame of the artificial bone, but can ensure the telescopic deformation property of the artificial bone, and the diameter of the carbon material pipe casing is slightly larger than the cross section of the carbon fiber composite spring-like frame, thus ensuring that the carbon fiber composite spring-like frame still has certain bending deformation property so as to meet the practical application requirements.

The carbon fiber composite plate bowel is provided with a plurality of sutural holes. The sutural holes are mainly used for fixation of the artificial bone during implantation.

Preferably, the carbon fiber composite plate dowel consists of a braided structure woven from carbon fibers and a pyrolytic carbon coating, a silicon carbide coating or a pyrolytic carbon/silicon carbide mixed coating on a surface thereof. The braided structure woven from the carbon fibers can ensure the mechanical property of the plate dowel.

Preferably, when the carbon fiber composite plate dowel penetrates through the cavity of the carbon fiber composite spring-like frame, since the length of the carbon fiber composite plate dowel is not less than the length of the carbon fiber composite spring-like frame, both ends or one end of the carbon fiber composite plate dowel are or is exposed. An exposed part of the plate dowel is mainly used as a connecting end of the artificial bone and tissues, and a part of the plate dowel penetrating through the cavity of the carbon fiber composite spring-like frame provides a mechanical support for the carbon fiber composite spring-like frame. The size of the plate dowel is generally matched with the size of the cavity of the carbon fiber composite spring-like frame, which can be understood by those skilled in the art.

Preferably, the volume density of the carbon fiber composite artificial bone is 0.8 $g/cm^3$-2.0 $g/cm^3$. The carbon fiber composite artificial bone has the characteristic of light weight.

The invention also provides a preparation method of the carbon fiber composite artificial bone, including the following steps:

1) twisting a plurality of carbon fibers into carbon fiber ropes, weaving at least three carbon fiber ropes into carbon fiber braids, and winding the carbon fiber braids onto a rod-shaped mold in parallel in a clockwise or counterclockwise direction to form a spring-like carbon fiber preform;

2) densifying the spring-like carbon fiber preform by chemical vapor infiltration and/or liquid impregnation to obtain a carbon fiber spring-like frame blank;

3) removing the carbon fiber spring-like frame blank from the rod-shaped mold, and then placing the carbon fiber spring-like frame blank in vacuum or protective atmosphere for high-temperature purification treatment to obtain the carbon fiber spring-like frame;

or placing the carbon fiber spring-like frame blank in vacuum or protective atmosphere for high-temperature purification treatment, and then removing the rod-shaped mold to obtain the carbon fiber spring-like frame;

4) preparing the pyrolytic carbon coating, the silicon carbide coating or the pyrolytic carbon/silicon carbide mixed coating on the surface of the tubular carbon fiber spring-like frame to obtain the carbon fiber composite spring-like frame; and 5) inserting the carbon fiber composite plate dowel into one end or both ends of the cavity of the carbon fiber composite spring-like frame, or penetrating the carbon fiber composite plate dowel through the cavity of the carbon fiber composite spring-like frame to obtain the artificial bone through combination of the carbon fiber composite spring-like frame and the carbon fiber composite plate dowel;

or combining the carbon fiber composite spring-like frame with the carbon fiber composite plate dowel, and then sleeving the carbon material pipe casing over the carbon fiber composite spring-like frame to obtain the artificial bone.

Preferably, each of the carbon fiber rope is formed by twisting of at least 1 k carbon fibers, and k represents one thousand.

Preferably, the rod-shaped mold is made of a carbon material or a material capable of generating a carbon material at a high temperature. By adopting the carbon material for the mold, it can be ensured that the carbon fiber material will not deform or collapse in a subsequent carbonization process.

Preferably, a cross section of the rod-shaped mold is circular, D-shaped, oval, pea-shaped, or square. The size and shape of the cross section of the mold can be adjusted arbitrarily according to the actual situation.

Preferably, a temperature for the high-temperature purification treatment is 1200° C.-2600° C., and heat preservation time is 2 h-15 h.

Preferably, a single carbon fiber braid or a plurality of carbon fiber braids may be used in the process of braiding the carbon fiber braids into the spring-like carbon fiber preform. The braiding density of the carbon fiber braids can be adjusted according to the actual situation, and the length of the spring-like carbon fiber preform can also be adjusted arbitrarily according to the actual situation.

Preferably, when the carbon fiber braids are used as the plate dowel, the carbon fiber braids are mechanically punched to form the sutural holes.

The carbon fiber of the invention is polyacrylonitrile-based carbon fiber or viscose-based, asphalt-based, phenolic-based carbon fiber.

A preparation method of the carbon fiber composite plate bowel in the invention includes:
1) twisting a plurality of carbon fibers into carbon fiber ropes, and weaving at least three carbon fiber ropes into carbon fiber braids;
2) densifying the carbon fiber braids by chemical vapor infiltration and/or liquid impregnation;
3) placing the densified carbon fiber braids in vacuum or protective atmosphere for high-temperature purification treatment; and
4) preparing the pyrolytic carbon coating, the silicon carbide coating or the pyrolytic carbon/silicon carbide mixed coating on surfaces of the carbon fiber braids.

The carbon fiber braids can be mechanically punched in any one of the above steps 1) to 4).

A chemical vapor infiltration process in the invention is as follows: putting the spring-like carbon fiber preform into a vacuum furnace, so that after pyrolysis of an introduced carbon-containing gas source (natural gas, methane, propylene or the like) at a temperature of 800° C.-1300° C., chemical vapor deposition is performed in the spring-like carbon fiber preform, and after 50 h-300 h, the carbon fiber spring-like frame blank is prepared.

A liquid impregnation densification process in the invention is as follows: subjecting the carbon fiber spring-like preform to densification treatment including vacuum pressure impregnation of resin (furan, phenolic aldehyde, furfural acetone and the like) or asphalt (graphite asphalt and coal asphalt), curing treatment and carbonization (resin: 1000° C., normal pressure; asphalt: 800° C., 100 MPa). Impregnation pressure is 1.0 MPa-5.0 MPa and impregnation time is 2 h-10 h. A curing temperature is 160° C.-230° C., and curing time is 10 h-50 h. Carbonization time is 2 h-20 h.

The pyrolytic carbon coating in the invention is prepared as follows: (1) carbon source gas: natural gas, methane, propylene or the like; (2) deposition temperature: 900° C.-1300° C.; (3) deposition time: 10 h-100 h.

The silicon carbide coating in the invention is prepared as follows: (1) raw materials: methyltrichlorosilane and hydrogen; (2) deposition temperature: 900° C.-1200° C.; (3) deposition time: 10 h-120 h.

The pyrolytic carbon/silicon carbide mixed coating in the invention is prepared as follows: firstly preparing the pyrolytic carbon coating and then preparing the silicon carbide coating according to the above methods.

Beneficial Effects of the Invention

Beneficial Effects

Compared with the Prior Art, the Technical Scheme of the Invention has the Following Beneficial Effects 1) The carbon fiber composite artificial bone of the invention is made of the carbon/carbon composite, and the carbon/carbon composite has the characteristics of good biocompatibility, light weight, mechanical property similar to that of human bones, good fatigue resistance and strong designability, and can avoid the artifacts in medical images.

2) The carbon fiber composite artificial bone of the invention has a special structure, including the special "spring-like" frame and the braid-shaped plate dowel with relatively good mechanical property; the spring-like frame endows the artificial bone with good elastic deformation property, so that the artificial bone can be bent at 360° arbitrarily. The carbon fiber composite plate dowel is arranged at one end or both ends of the cavity of the frame or penetrates through the cavity of the frame. The plate dowel is used as a connecting end of the artificial bone and other tissues and is beneficial to the fixation of the artificial bone, and when arranged in a penetrating mode, the plate dowel can also improve the mechanical property of the artificial bone and enhance the deformation recovery capability of the artificial bone, and the artificial bone with this structure can realize some functions of cartilage and bending modeling. The carbon fiber composite artificial bone may be further provided with the carbon material pipe casing to prevent tissues from growing into the spring-like frame of the artificial bone after the artificial bone is transplanted into the human body so as to affect the deformation capability of the artificial bone.

3) The carbon fiber composite frame of the invention is woven by the carbon fibers, specifically, the carbon fibers are twisted into the carbon fiber ropes first and then woven into the carbon fiber braids, and finally the carbon fiber braids are made into the spring-like carbon fiber preform. A prepared spring-like structure not only maintains light weight, good mechanical property and high toughness of the carbon fibers, but also has good elastic deformation property similar to a spring. A tensile rigidity coefficient of the spring-like frame in the prepared artificial bone is 0.1 kg/mm-5 kg/mm, an elongation rate is 10%-100%, and a bending deformation angle is 0°-360°, while the conventional carbon/carbon composite is a block which cannot realize elastic deformation.

4) The carbon fiber composite artificial bone of the invention combines the carbon fiber weaving technology with the profiling technology, and the method is easy to operate, and beneficial to forming and large-scale production.

DETAILED DESCRIPTION

The Embodiments of the Invention

Figure 1:
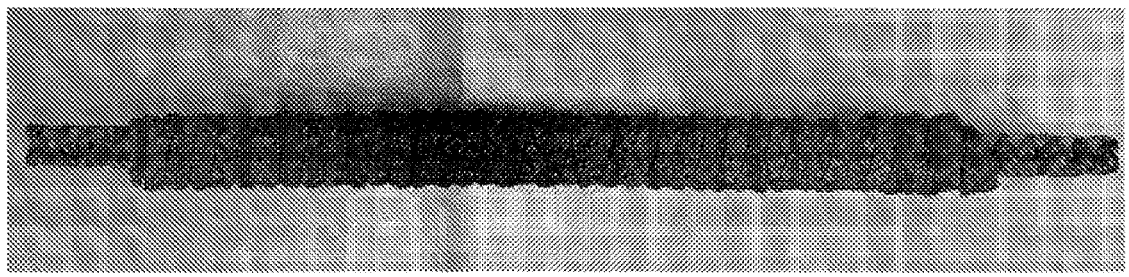
FIG. 1 is a photograph of a carbon fiber composite artificial bone prepared in Embodiment 1.
Figure 2:
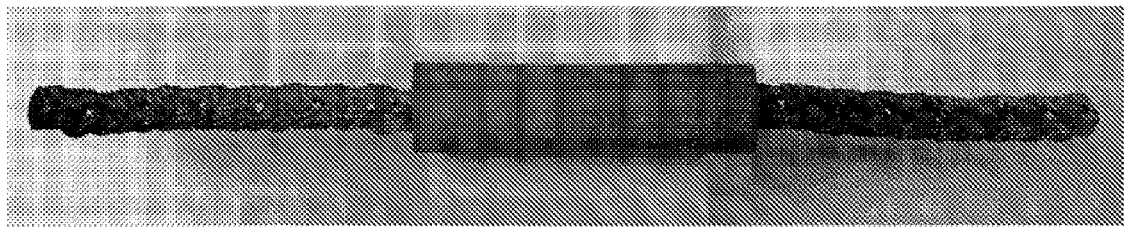
FIG. 2 is a photograph of a carbon fiber composite artificial bone prepared in Embodiment 3 (provided with a pipe casing).

The following embodiments are intended to further illustrate the invention and are not intended to limit the scope of protection of the claims of the invention.

Embodiment 1

1) Firstly, 12 k polyacrylonitrile-based carbon fibers are twisted into carbon fiber ropes. Then three 12 k carbon fiber ropes are woven into carbon fiber braids. The carbon fiber braids are tightly wound onto a carbon material mold with a D-shaped cross section (the cross section size is the same as that of a human rib) in parallel in a clockwise direction to form a spring-like carbon fiber preform.

2) The tubular carbon fiber preform is placed in natural gas atmosphere, and chemical vapor deposition is performed for 200 h at a temperature of 1100° C. Thus, a carbon fiber spring-like frame blank with the blank density of 1.2 g/cm$^3$ is obtained.

3) The carbon fiber spring-like frame blank is removed from the rod-shaped mold, and then is placed in argon protective atmosphere and heated to 2200° C. with heat preservation time of 10 h for purification treatment. Thus, a carbon fiber spring-like frame is obtained.

4) The carbon fiber spring-like frame is subjected to chemical vapor deposition at 1150° C. for 50 h by using methane as a carbon source, so as to prepare a pyrolytic carbon coating. Thus, a carbon fiber composite spring-like frame is obtained.

5) Carbon fiber composite plate dowels with punched surfaces are inserted into both ends of a hollow part of the carbon fiber composite spring-like frame respectively. Each of the plate dowels at both ends is about 10 mm and serves as a connecting end. The total length of the carbon fiber composite spring-like frame and the plate dowels are similar to that of a rib, and thus, an artificial rib is obtained. The carbon fiber composite plate dowel is prepared as follows: three 6 k polyacrylonitrile-based carbon fibers are twisted into carbon fiber ropes, a plurality of carbon fiber ropes are woven into carbon fiber braids with the size being controlled to be similar to the size of the cross section of the mold, the length is directly determined according to the actual situation, and then densification is performed according to a conventional method to prepare coatings.

A tensile rigidity coefficient of the spring-like frame in the artificial bone prepared in the present embodiment is 0.2 kg/mm, an elongation rate is 60%, and a bending deformation angle can reach 180°.

Embodiment 2

1) 12 k polyacrylonitrile-based carbon fibers and 6 k polyacrylonitrile-based carbon fibers are twisted into carbon fiber ropes respectively. One 12 k polyacrylonitrile-based carbon fiber rope and two 6 k polyacrylonitrile-based carbon fiber ropes are woven into a carbon fiber braid. Two carbon fiber braids are wound onto a carbon material mold with a rectangular cross section (the cross section size is similar to that of the human rib) in parallel in a clockwise direction to form a spring-like carbon fiber preform.

2) The carbon fiber spring-like preform is subjected to densification treatment including vacuum pressure impregnation, curing treatment and carbonization by using phenolic resin as an impregnant. The main parameters are as follows: impregnation pressure: 3.0 MPa, impregnation time: 5 h, curing temperature: 200° C., curing time: 20 h, carbonization temperature: 1000° C., and carbonization time: 4 h, so that after 3 cycles, a carbon fiber spring-like frame blank with the blank density of 1.5 g/cm$^3$ is obtained.

3) The carbon fiber spring-like frame blank is removed from the rod-shaped mold, and then is placed in argon protective atmosphere and heated to 2000° C. with heat preservation time of 12 h for purification treatment. Thus, a carbon fiber spring-like frame is obtained.

4) The carbon fiber spring-like frame is subjected to chemical vapor deposition at 1100° C. for 30 h by using methyltrichlorosilane and hydrogen as raw materials, so as to prepare a silicon carbide coating on a surface of the carbon fiber spring-like frame. Thus, a carbon fiber composite spring-like frame is obtained.

5) Carbon fiber composite plate dowels with punched surfaces penetrate through a hollow part of the carbon fiber composite spring-like frame. One end is exposed by about 20 mm and serves as a connecting end. The total length of the carbon fiber composite spring-like frame and the plate dowel is similar to that of a rib, and thus, an artificial rib is obtained. The carbon fiber composite plate dowel is prepared as follows: 48 k polyacrylonitrile-based carbon fibers are twisted into carbon fiber ropes, a plurality of 48 k carbon fiber ropes are woven into carbon fiber braids with the size being controlled to be similar to the size of the cross section of the mold, the length is directly determined according to the actual situation, and then densification is performed according to a conventional method to prepare coatings.

A tensile rigidity coefficient of the spring-like frame in the artificial bone prepared in the present embodiment is 1 kg/mm, an elongation rate is 40%, and a bending deformation angle can reach 60°.

Embodiment 3

1) Firstly, three 3 k polyacrylonitrile-based carbon fibers are twisted into carbon fiber ropes. Then five carbon fiber ropes are woven into carbon fiber braids. Three carbon fiber braids are tightly wound onto a carbon material mold with a rectangular cross section (the cross section size is similar to a human rib) in parallel in a counterclockwise direction to form a spring-like carbon fiber preform.

2) The tubular carbon fiber preform is subjected to chemical vapor deposition at 900° C. for 120 h by using propylene as a carbon source and nitrogen as a diluent gas. Then densification treatment including vacuum pressure impregnation, curing treatment and carbonization are performed by using phenolic resin as an impregnant. The main parameters are as follows: impregnation pressure: 4.0 MPa, impregnation time: 3 h, curing temperature: 220° C., curing time: 15 h, carbonization temperature: 950° C., carbonization time: 6 h. Thus, after 2 cycles of liquid phase impregnation, a carbon fiber spring-like frame blank with the blank density of 1.8 g/cm$^3$ is obtained.

3) The carbon fiber spring-like frame blank is removed from the rod-shaped mold, and then is placed in argon protective atmosphere and heated to 2100° C. with heat preservation time of 10 h for purification treatment. Thus, a carbon fiber spring-like frame is obtained.

4) A surface of the tubular frame is subjected to chemical vapor deposition at 1120° C. for 30 h by using methane as a carbon source. Then chemical vapor deposition is performed at 1100° C. for 20 h by using methyltrichlorosilane and hydrogen as raw materials, so as to prepare a pyrolytic carbon and silicon carbide composite coating. Thus, a carbon fiber composite spring-like frame is obtained.

5) A carbon fiber composite plate dowel with a punched surface is inserted into one end of a hollow part of the carbon fiber composite spring-like frame. The plate dowel is about 40 mm in length and serves as a connecting end. The total length of the carbon fiber composite spring-like frame and the plate dowel is similar to that of a rib, and thus, an artificial rib is obtained. The carbon fiber composite plate dowel is prepared as follows: 24 k polyacrylonitrile-based carbon fibers are twisted into carbon fiber ropes, a plurality of 24 k carbon fiber ropes are divided into three strands to be woven into carbon fiber braids with the size being controlled to be similar to the size of the cross section of the mold, the length is directly determined according to the actual situation, and then densification is performed according to a conventional method to prepare coatings.

A tensile rigidity coefficient of the spring-like frame in the artificial bone prepared in the present embodiment is 4 kg/mm, an elongation rate is 20%, and a bending deformation angle can reach 30°. The bending deformation angle can reach 5° by sleeving a carbon material pipe casing over the artificial rib.

What is claimed is:

1. A carbon fiber composite artificial bone, comprising a carbon fiber composite spring-like frame and a carbon fiber composite plate dowel, wherein the carbon fiber composite plate dowel penetrates through a cavity of the carbon fiber composite spring-like frame, wherein the carbon fiber composite spring-like frame comprises a carbon fiber spring-like frame and a pyrolytic carbon coating, a silicon carbide coating or a pyrolytic carbon/silicon carbide mixed coating on a surface of the carbon fiber spring-like frame, and the carbon fiber spring-like frame is of a spring-like structure woven from carbon fibers, wherein the carbon fiber spring-like frame comprises woven carbon fiber braids that wind in a clockwise direction or a counterclockwise direction and spirally extend in an extending direction of the carbon fiber spring-like frame, each of the woven carbon fiber braids comprise at least three woven carbon fiber ropes, and each of the woven carbon fiber ropes comprise a plurality of twisted carbon fibers, wherein the carbon fiber composite plate dowel comprises a braided structure woven from carbon fibers and a pyrolytic carbon coating, a silicon carbide coating or a pyrolytic carbon/silicon carbide mixed coating on a surface of the braided structure, wherein the carbon fiber spring-like frame has 0.1-5 kg/mm of a tensile rigidity coefficient.

2. The carbon fiber composite artificial bone according to claim 1, wherein a carbon material pipe casing is arranged outside the carbon fiber composite spring-like frame, and a cross section of the carbon fiber composite spring-like frame is circular, oval, D-shaped, pea-shaped or square.

3. The carbon fiber composite artificial bone according to claim 1, wherein the carbon fiber composite plate bowel is provided with a plurality of sutural holes.

4. The carbon fiber composite artificial bone according to claim 1, wherein when the carbon fiber composite plate dowel penetrates through the cavity of the carbon fiber composite spring-like frame, a length of the carbon fiber composite plate dowel is not less than a length of the carbon fiber composite spring-like frame, and both ends or one end of the carbon fiber composite plate dowel are or is exposed.

5. The carbon fiber composite artificial bone according to claim 1, wherein the volume density of the carbon fiber composite artificial bone is 0.8 g/cm$^3$-2.0 g/cm$^3$.

* * * * *